United States Patent [19]

Minami et al.

[11] 3,972,616
[45] Aug. 3, 1976

[54] APPARATUS FOR DETECTING THE DEFECTS OF THE MASK PATTERN USING SPATIAL FILTERING

[75] Inventors: Masana Minami, Kawasaki; Hidekazu Sekizawa, Yokohama, both of Japan

[73] Assignee: Tokyo Shibaura Electric Co., Ltd., Japan

[22] Filed: June 27, 1975

[21] Appl. No.: 590,933

[30] Foreign Application Priority Data
Sept. 9, 1974 Japan.............................. 49-102993

[52] U.S. Cl.................................. 356/71; 350/81; 350/162 SF; 356/237; 356/239
[51] Int. Cl.².................... G06K 9/08; G01N 21/16; G01N 21/32
[58] Field of Search..................... 356/71, 237, 239; 350/162 SF; 250/572

[56] References Cited
UNITED STATES PATENTS

| | | | |
|---|---|---|---|
| 3,614,232 | 10/1971 | Mathisen | 356/239 |
| 3,658,420 | 4/1972 | Axelrod | 356/239 |
| 3,738,752 | 6/1973 | Heinz et al. | 356/239 |

*Primary Examiner*—Vincent P. McGraw
*Attorney, Agent, or Firm*—Oblon, Fisher, Spivak, McClelland & Maier

[57] ABSTRACT

Two kinds of light sources, one of which emits a coherent light and the other of which emits incoherent light, are provided. The coherent light and incoherent light respectively emitted from the two different kinds of light sources, proceed on the same optical axis. A photomask, such as for an integrated-circuit, or other objects, which have linear straight line features and nonlinear defects, are simultaneously illuminated by the coherent light and incoherent light.

The two kinds of light which pass through the photomask or other objects are transformed into a Fourier-transform pattern by a transform lens. A spatial filter, having a plurality of arms which extend in predetermined directions from the center thereof, is provided on the focal plane of the transform lens.

The spatial filter suppresses the passing of coherent light having information of the linear straight line features. The coherent light which has information of the defects of the photomask is not suppressed by the spatial filter. The coherent light and incoherent light passing through the spatial filter are directed to an image plane.

As a result thereof, an image of the photomask or other object, obtained by the incoherent light and an image of the defects of the photomask or other objects obtained by the coherent light, are simultaneously projected on each other on the image plane.

10 Claims, 10 Drawing Figures

APPARATUS FOR DETECTING THE DEFECTS OF THE MASK PATTERN USING SPATIAL FILTERING

BACKGROUND OF THE INVENTION

1. Field of the Invention

This invention relates generally to an apparatus for detecting the defects of an object, and more particularly, to an apparatus for detecting the defects of a photomask or object having linear straight line features and nonlinear defects, by using coherent light and incoherent light.

2. Description of the Prior Art

In the past, the detection of the defects of an object such as a mask pattern of a photomask for integrated-circuits was carried out by the visual observation of a human operator looking through a microscope. While somewhat satisfactory, it was difficult to distinguish the difference between defects and a proper mask pattern, as the chip-size enlarges and as the pattern becomes fine. Under such considerations, the human operator can rapidly become fatigued and apt to make misdetections. This, in turn, results in a lowering of the accuracy of detection.

In order to solve the above-mentioned problem, some methods for automatic detection have been suggested. One such method utilizes the directional character of the pattern. Thus, a mask pattern with linear straight line features formed by a combination of straight line components, is illuminated by coherent light, and a spatial filter for cutting the linear straight line features of the mask pattern, is provided at the Fourier-transform plane. This method is known as Watkins' method, and is described in the "PROCEEDINGS OF IEEE," April, 1972, pages 407 – 449. Again, while somewhat satisfactory, the defects detected by this method do not include position-information indicating where the defect exists in the mask pattern. However, whether a detected defect is important, or can be neglected, depends upon the position of the defect.

Consequently, a need exists for an apparatus for detecting the defects of an object, such as a photomask, which can conveniently and automatically judge whether a detected defect is an important one or not.

SUMMARY OF THE INVENTION

Accordingly, it is an object of the present invention to provide a new and improved apparatus for detecting and locating the defects of an object having linear straight line features and nonlinear defects.

Another object of the present invention is to provide a new and improved apparatus for detecting the defects of an object such as a photomask in which a coherent light source and an incoherent light source, which respectively emit different colored light, are located such that defects in a photomask can be detected and the position of the detected defects located.

Briefly, according to this invention, the foregoing and other objects are attained by the provision of an apparatus for detecting the defects of an object which includes a coherent light source and an incoherent light source. Means are provided for directing on the same optical axis coherent light emitted from a coherent light source and incoherent light emitted from an incoherent light source to the object having linear straight-line features and nonlinear defects, a lens for condensing the coherent light and the incoherent light respectively permeated through or reflected from the object, and a spatial filter located on the focal plane of the condensing lens for filtering the coherent light having information of the linear straight line features.

BRIEF DESCRIPTION OF THE DRAWINGS

This invention can be more fully understood from the following detailed description when considered in connection with the accompanying drawings, wherein:

FIGS. 4A and 4B are also diagrams showing examples of output images of the object and the defects of the object, wherein FIG. 4A shows an image obtained by incoherent light, and FIG. 4B shows an image obtained by coherent light;

DETAILED DESCRIPTION OF THE PREFERRED EMBODIMENTS

Figure 1:
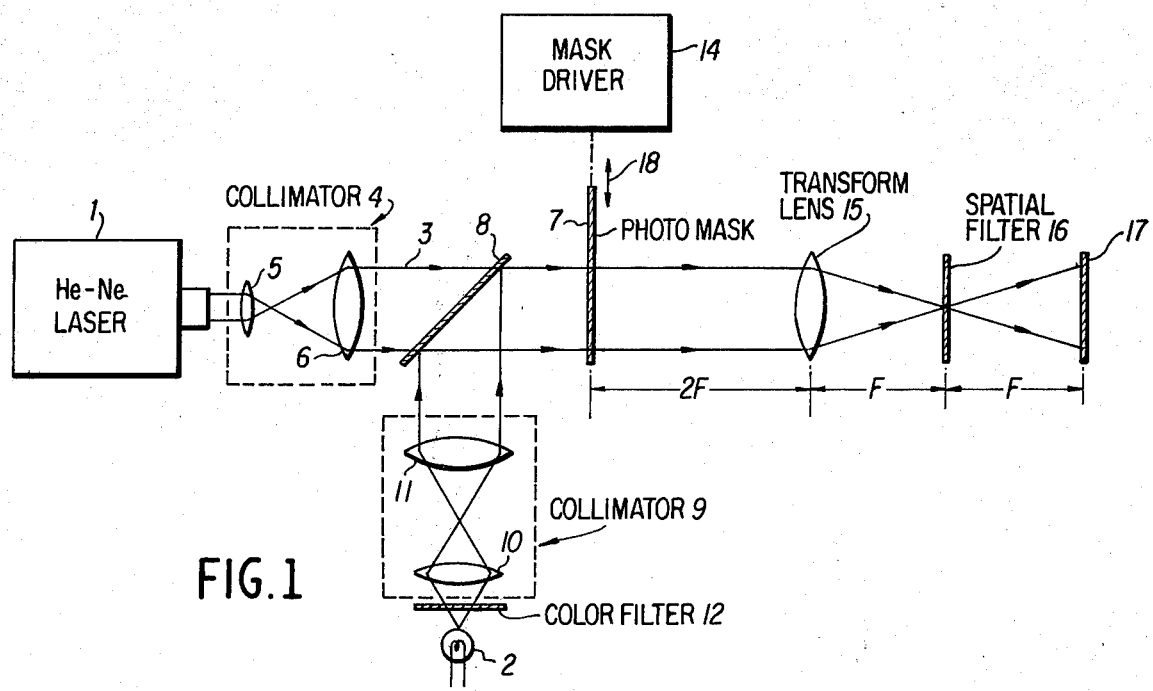
FIG. 1 is a diagram showing a preferred embodiment of an apparatus for detecting the defects of an object such as a photomask in accordance with the present invention.

Referring now to the drawings, wherein like reference numerals refer to or designate identical or corresponding parts throughout the several views, and more particularly to FIG. 1 thereof wherein a coherent light source 1 and an incoherent light source 2 are shown as being provided. A Helium-Neon (He—Ne) laser, for example, is used for the coherent light source 1, and an incandescent lamp, for example, is used for the incoherent light source 2. Coherent light emitted from the coherent light source 1 is transformed into parallel light 3 of a desired diameter by a collimator 4 which includes two lenses 5 and 6. The parallel light 3 irradiates an object such as a photomask 7 for an integrated circuit through a half mirror 8.

Additionally, incoherent light emitted from the incoherent light source 2 is applied to a collimator 9, which includes lenses 10 and 11, through a color filter 12, and is transformed into parallel light 13. The parallel light 13 irradiates the photomask 7 through the half mirror 8. Accordingly, coherent light and incoherent light are applied to the photomask 7 along the same optical axis. The photomask 7 is appropriately moved by a mask driver 14 in order to illuminate a desired part of the photomask 7.

As mentioned above, if an He—Ne laser is used in the present embodiment for the coherent light source 1, then it is desirable to use the color filter 12 which will pass a different colored light from that of the coherent light.

Therefore, when the He—Ne laser is used for the coherent light source 1 and a filter passing green color is used for the color filter 12, red-colored coherent light and green-colored incoherent light will be applied on the same optical axis to the photomask 7. The coherent light and incoherent light which are two different colored lights are, respectively, permeated through the photomask 7 to provide information of the photomask 7 and are condensed by a transform lens 15 provided in an optical filtering system.

The transform lens 15 is located at a position being 2F from the photomask 7, where F indicates a focal length of the transform lens 15. The transform lens 15 acts as a Fourier-transform lens against the coherent light permeated through the photomask 7.

Accordingly, coherent light having information of the photomask 7 is transformed into a Fourier-transform pattern by the transform lens 15, and a spectrum distribution on the Fourier-transform plane changes according to the Fourier-transform of the photomask 7.

Figure 2A:
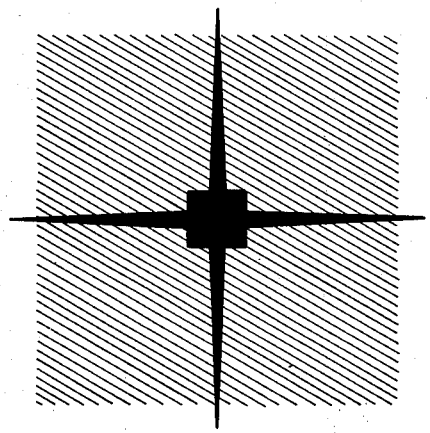
FIGS. 2A and 2B are diagrams showing an intensity distribution of coherent light permeated through the object of a filtering plane.
Figure 2B:
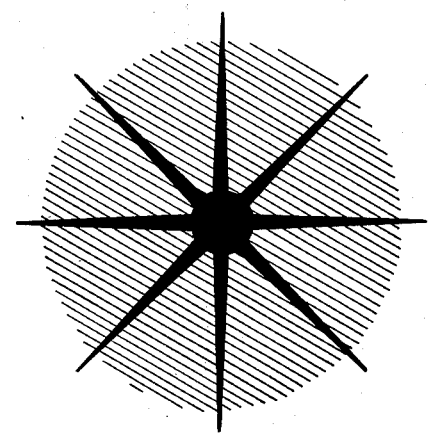

FIG. 2A shows a spectrum distribution on the Fourier-transform plane in the case wherein the photomask 7 is formed by a combination of longitudinal straight lines and cross straight lines, and FIG. 2B shows a spectrum distribution on the Fourier-transform plane in the case wherein the photomask 7 is formed by a combination of longitudinal straight lines, cross straight lines and diagonal straight lines.

In FIGS. 2A and 2B, the dark-colored parts indicate a Fourier-spectrum of a proper mask pattern which does not include any defects and the light-colored parts show a spectrum of defects of the photomask 7 such as dust, cracks or scratches. The spectrum of the defects has such an extent because the defects have essentially no specific directional character in themselves.

Figure 3A:
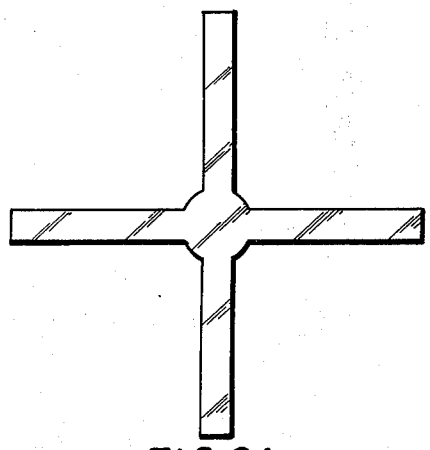
FIGS. 3A and 3B are diagrams showing the shapes of spatial filters which can be used with the present invention.
Figure 3B:
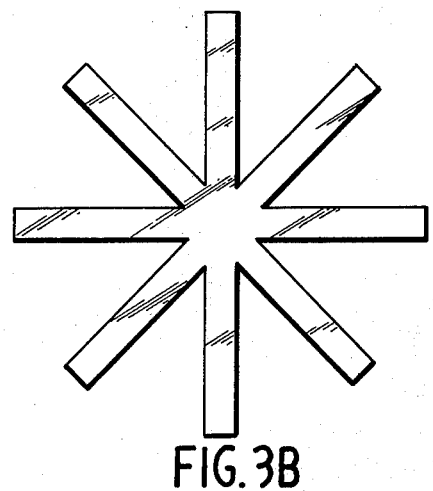

Referring now, again, to FIG. 1, a spatial filter 16 as shown in FIGS. 3A and 3B is provided and located at the focal plane of the transform lens 15. The spatial filter 6 is shaped according to the Fourier-spectrum distribution of the proper mask pattern, and has a wavelength selectivity. As a result, the coherent light having information of the proper mask pattern is prevented from passing through the spatial filter 16, and only the image of the defects is projected on a screen 17 located at a distance F from the spatial filter 16.

It should be noted that the directional distribution of the incoherent light permeated through the mask pattern 7 is not as clear as that of the coherent light. Therefore, since the spatial filter 16 does not prevent the passing of incoherent light, the image of the photomask 7, which includes the proper mask pattern and defects is projected on the screen 17 by the incoherent light.

Generally, it is presumed that the quality of incoherent image deteriorates because of the filtering effect of the spatial filter 16. However, as mentioned above, the wavelength of the coherent light and that of the incoherent light are different from each other, and the spatial filter 16 has wavelength selectivity. Accordingly, almost all of the incoherent light is passed by the spatial filter 16. Thus, when green-colored incoherent light and red-colored coherent light are used for the apparatus of this invention, the defects indicated by the red color and the mask pattern indicated by green color are simultaneously projected one upon another on the screen 17. It is easy to detect the defects of the photomask 7 because the photomask is indicated by the green color and the defects therein are indicated by the red color.

After finishing the detection of a part or portion of the photomask 7, the photomask 7 is moved in the direction of arrow 18 by the mask driver 14 so as to detect another part of the photomask 7. It is clear that the movement of the photomask 7 does not affect the detecting function of the present invention.

Figure 4A:
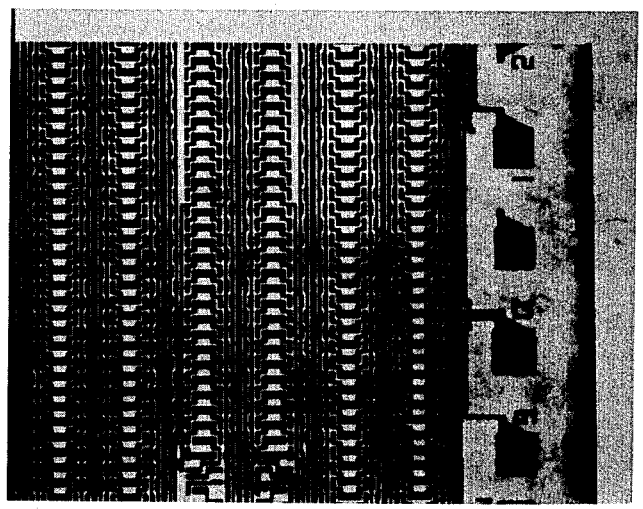

FIG. 4A shows an image of the photomask 7 which is projected on the screen 17 by incoherent light. This image is projected by a green color. The defects existing in this image are indicated by circle.

Figure 4B:
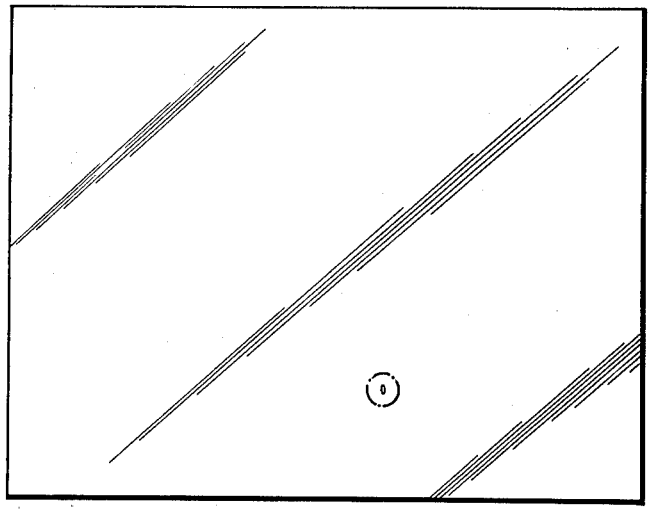

FIG. 4B shows an image of the defects of the photomask 7 which are projected on the screen 17. The defect indicated by a circle is projected by a red color. In actual use, the two images of FIGS. 4A and 4B are projected upon each other.

Therefore, the defects indicated by the red color are clearly projected on the mask pattern indicated by the green color. Accordingly, with the present invention, it is easy to detect not only the defects, but the position of the defects, and to judge whether the detected defects are important or can be neglected. Additionally, position among the two images is complete and accurate because the coherent light and the incoherent light are applied to the photomask 7 on the same optical axis.

Furthermore, the intensity of the coherent light is controlled by the coherent light source 1, and in the same manner, the intensity of the coherent light is controlled by the incoherent light source 2. Therefore, the relative ratio of intensity of the coherent image to that of the incoherent image is changeable and is adjusted so as to enable suitable detection of the defects.

Figure 5:
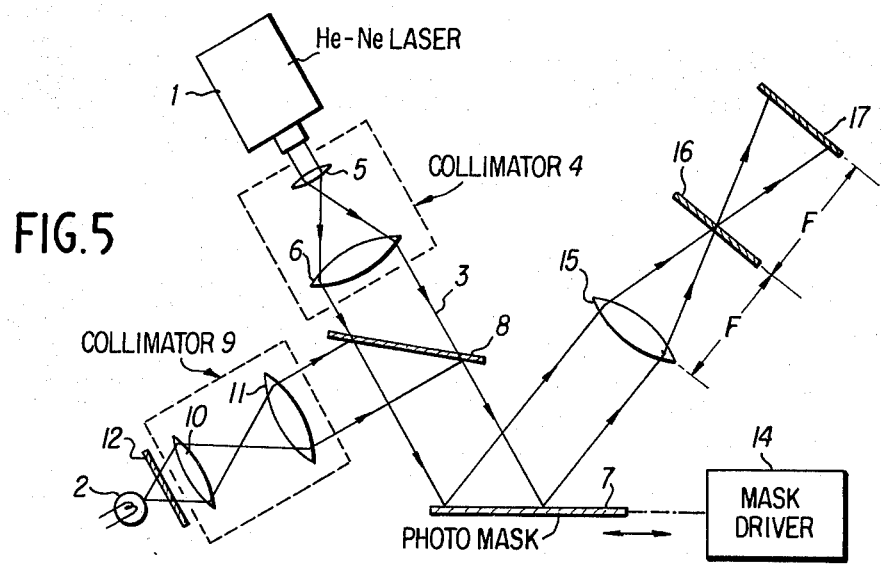
FIG. 5 is a diagram showing another preferred embodiment of an apparatus for detecting the defects of an object such as a wafer in accordance with the present invention.

FIG. 5 shows another and alternative preferred embodiment of the present invention. The apparatus shown in FIG. 5 is suitable to use when the coherent light and the incoherent light do not sufficiently permeate through the object 7 such as a wafer. Accordingly, under such circumstances coherent light emitted from the coherent light source 1 and incoherent light emitted from the incoherent light source 2 will diagonally irradiate the object 7 through the half mirror 8, and the reflective light utilized and directed to the transform lens 15. Such an arrangement is also particularly suitable for detecting defects of objects, such integrated components wherein light will reflect, but not permeate the object.

Figure 6:
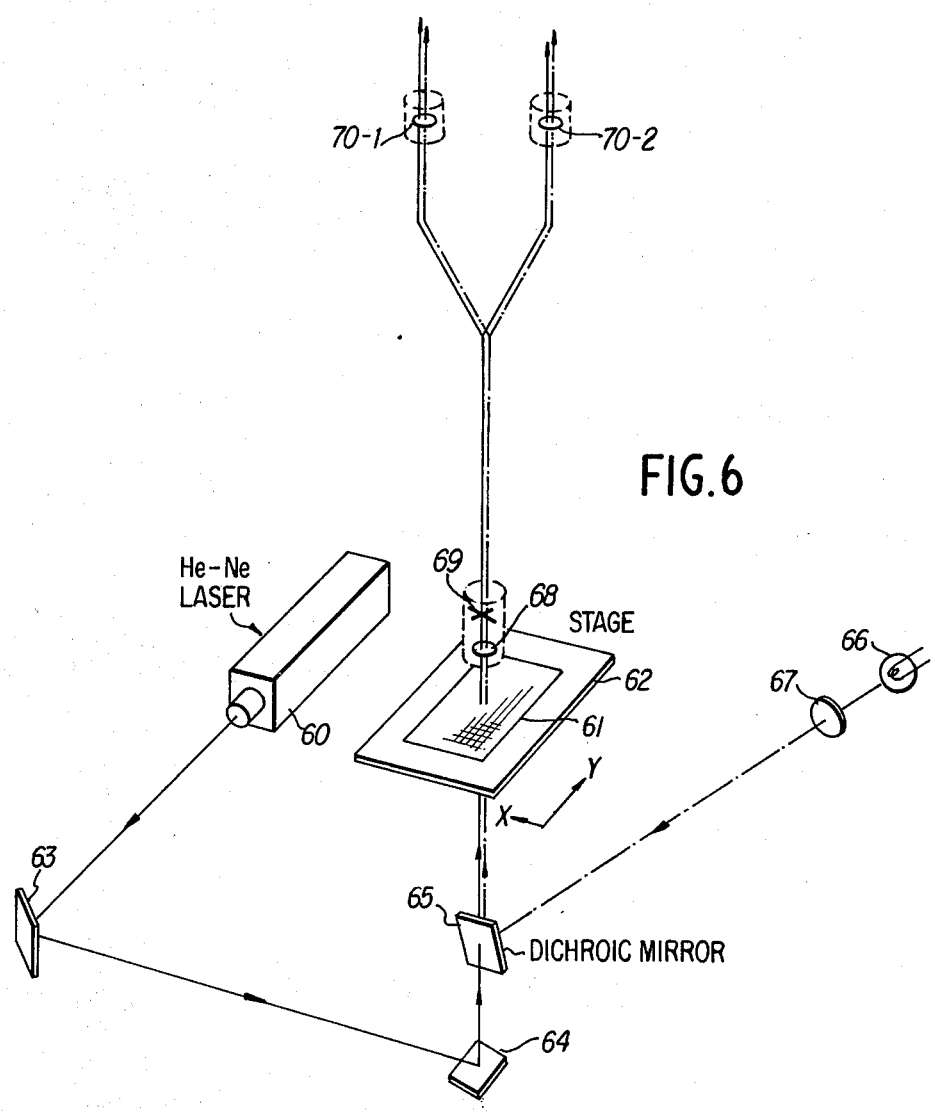
FIG. 6 is a diagram showing an application of the present invention to a microscope.

FIG. 6 is a diagram showing an application of the present invention with a microscope. Coherent light (red-colored) emitted from a coherent light source 60 (He—Ne gas laser; power of 0.5 mV) irradiates a certain part of a mask 61 set on the stage 62 of a microscope through total reflection mirrors 63 and 64 and a dichroic mirror 65. On the other hand, incoherent light emitted from an incoherent light source 66 (incandescent lamp) irradiates the same part of the mask 61 through a lens 67 and the dichroic mirror 65. The dichroic mirror 65 reflects green color and permeates red and blue colors.

Consequently, the mask 61 is simultaneously illuminated by the red-colored coherent light and the green-colored incoherent light, on the same optical axis. The mask 61 is moved in the X and Y directions by the stage drive (not shown) of the microscope.

Subsequently, the coherent and incoherent lights permeated through the mask 61 are led to an objective lens 68 of the microscope. The objective lens 68 of the microscope comprises at least one lens. The rear focal plane of the object glass is out of the lens group. A spatial filter 69 such as shown in FIGS. 3A and 3B, is located on the rear focal plane of the object glass 68. The optical filter 69 and the objective lens 68 are placed within a common housing and the spatial filter 69 is fixed therein. As mentioned above, the spatial filter 69 serves to prevent the passing of coherent light having information of the linear straight line features of the proper mask pattern.

Coherent light having information of the defects and incoherent light having information of the linear straight line features and nonlinear defects are passed through the spatial filter 69 and applied to oculars 70-1 and 70-2 for viewing by a human operator. As a result thereof, an operator can easily detect the defects of the mask 61 and, furthermore, can judge where the defect in the mask pattern is located. Accordingly, operator fatigue is decreased and the efficiency of inspection increased.

Figure 7:
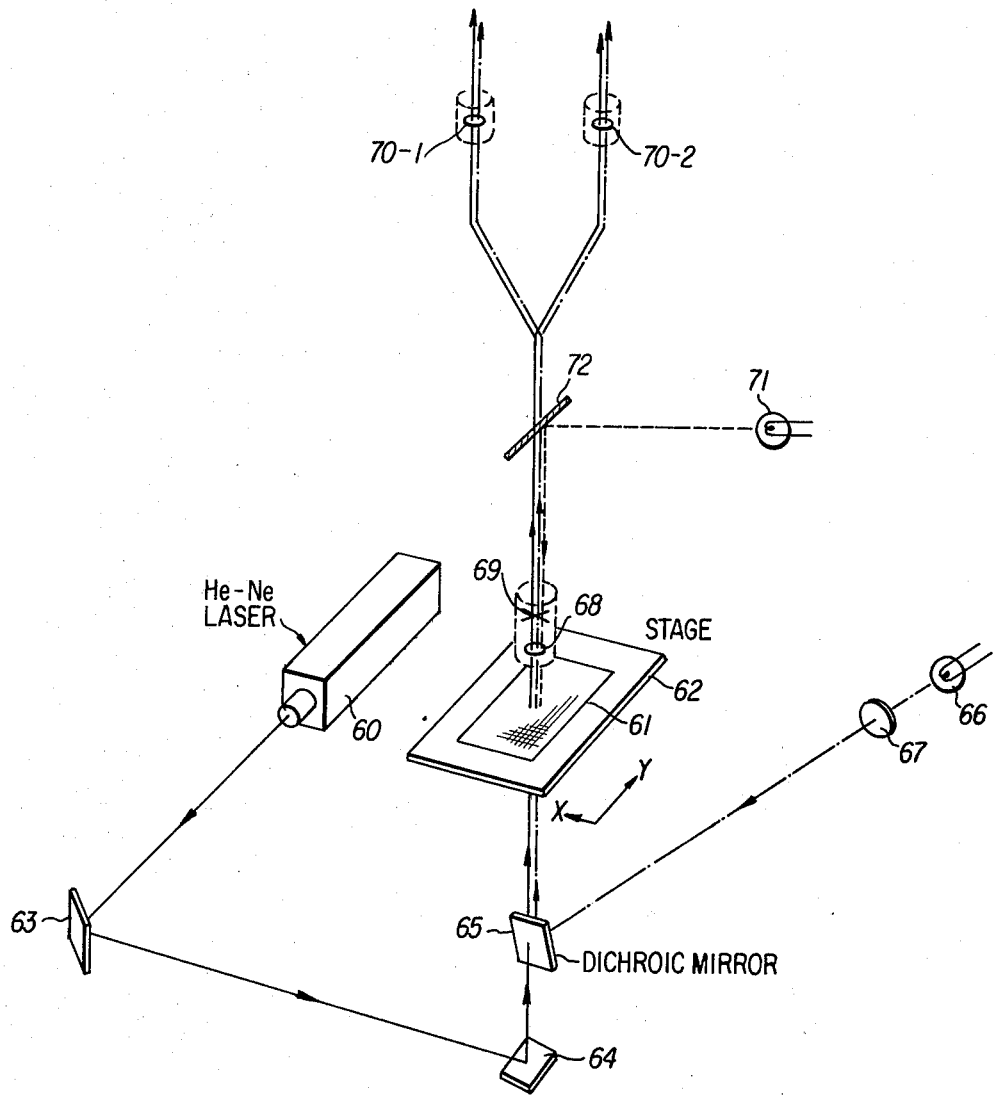
FIG. 7 is another diagram showing an application of the present invention to a microscope.

FIG. 7 shows another application of the present invention as used with a microscope. In this arrangement, another incoherent light source 71 and a half mirror 72 are provided. Incoherent light emitted from the incoherent light source 71 is applied to the mask 61 through the half mirror 72, the spatial filter 69 and the objective lens 68. Incoherent light reflected from the mask 61 is received by an operator through the objective lens 68, the spatial filter 69, the half mirror 72 and oculars 70-1 and 70-2.

According to this arrangement, the S-N ratio is improved since the incoherent image reflected to the operator suppresses the unwanted stray coherent light.

Obviously, numerous modifications of the present invention are possible in light of the above teachings.

For example, the output image can be taken as a picture by a vidicon or an ITV camera. When the output image is taken as a picture by a color camera, it is easy to detect the defects and the position thereof from the electric signals generated thereby.

Furthermore, with the present invention, it is possible to provide a coherent light source and an incoherent light source which emit the same colored light. In this case, the two lights can be alternately applied to the object or mask pattern. The output image is then converted into electric signals by a light-electric converter in accordance with the switching time of the two lights, and can be indicated by an indicator such as a TV by a different color from each other.

Therefore, it is to be understood that within the scope of the appended claims, the present invention may be practiced otherwise than as specifically described herein.

What is claimed as new and desired to be secured by letters patent of the United States is:

1. Apparatus for detecting defects of an object having linear straight line features and nonlinear defects comprising:
   a coherent light source for emitting coherent light;
   an incoherent light source for emitting incoherent light;
   a first collimator for collimating said coherent light to a prescribed light thickness;
   a second collimator for collimating said incoherent light to a prescribed light thickness;
   means for irradiating coherent light passed through said first collimator and incoherent light passed through said second collimator on the same optical axis to said object;
   a transform lens for transforming the intensity distribution of permeated light or reflected light of said object into a Fourier-transform pattern;
   a spatial filter located on the Fourier-transform plane of said transform lens, and for preventing the passing of coherent light having information of said linear straight line features of said object; and
   means for projecting a coherent image and an incoherent image respectively passed through said spatial filter on one another.

2. Apparatus for detecting defects of an object as in claim 1 wherein said object is a photomask.

3. Apparatus for detecting defects of an object as in claim 1 wherein a color filter is located between said incoherent light source and said second collimator.

4. Apparatus for detecting the defects of an object according to claim 1, wherein:
   said coherent light source is a laser emitting red colored coherent light.

5. Apparatus for detecting the defects of an object according to claim 3 wherein:
   said color filter prevents the passing of red-colored incoherent light.

6. Apparatus for detecting the defects of an object according to claim 1 wherein:
   said irradiating means comprises a half mirror.

7. Apparatus for detecting the defects of an object according to claim 1, wherein:
   said irradiating means comprises a dichroic mirror.

8. Apparatus for detecting the defects of an object according to claim 1, wherein:
   said spatial filter is formed by a plurality of arm portions extending in predetermined directions from the center thereof.

9. Apparatus for detecting the defects of an object according to claim 1, wherein:
   said transform lens and said spatial filter are placed in a housing for an objective lens of a microscope, and projecting means comprising an ocular of said microscope.

10. Apparatus for detecting the defects of an object according to claim 9 wherein:
   means for illuminating said mask pattern by incoherent light through said spatial filter is further provided.

* * * * *